United States Patent [19]

Olivier

[11] Patent Number: 5,759,224
[45] Date of Patent: Jun. 2, 1998

[54] DEVICE AND METHOD FOR THE CONTINUOUS TREATMENT OF WASTE BY MEANS OF FLY LARVAE

[76] Inventor: Paul A. Olivier, Handzamestraat, 159, B-8610 Handzame, Belgium

[21] Appl. No.: 697,314

[22] Filed: Aug. 22, 1996

[51] Int. Cl.⁶ .................. C05F 11/08; C12M 1/38
[52] U.S. Cl. .................. 71/9; 71/15; 71/21; 435/290.4
[58] Field of Search .................. 435/290.4; 71/9, 71/15, 21

[56] References Cited

U.S. PATENT DOCUMENTS 4,040,810  8/1977  Eby et al. .................. 71/21 X

*Primary Examiner*—Ferris Lander
*Attorney, Agent, or Firm*—Sughrue, Mion, Zinn, Macpeak & Seas, PLLC

[57] ABSTRACT

The invention relates to a devive and a method for the continuous treatment of putrescent waste in which the waste is eaten by fly larvae. The device comprises:

- a conveyor belt;
- a means to distribute the waste;
- a means for depositing fly larvae eggs onto the waste;
- a means for removing fly larvae from the waste and from the conveyor belt;
- a means for removing the waste from the conveyor belt.

27 Claims, 2 Drawing Sheets

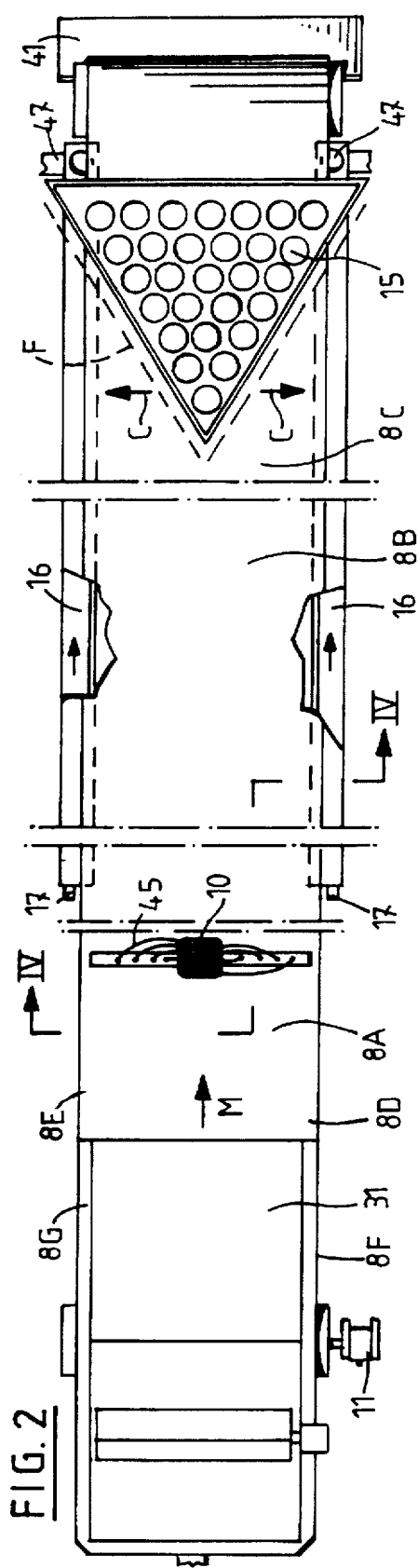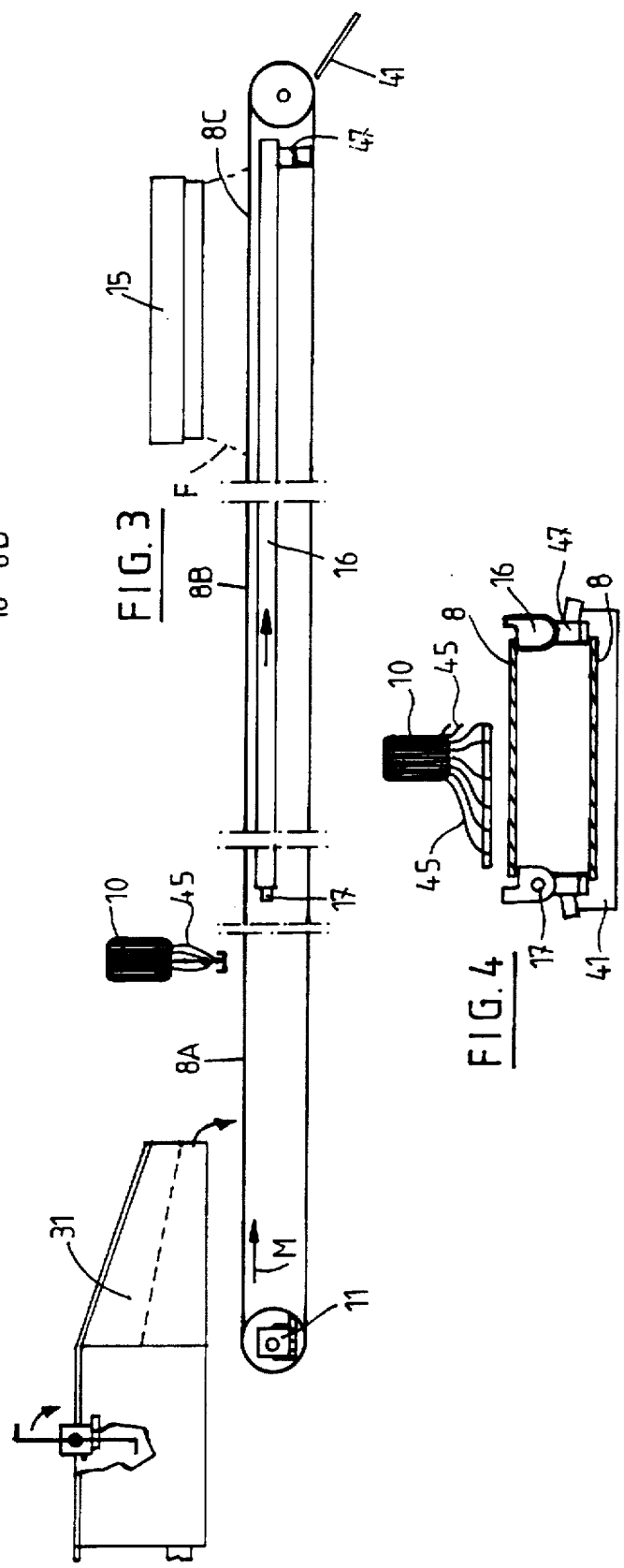

DEVICE AND METHOD FOR THE CONTINUOUS TREATMENT OF WASTE BY MEANS OF FLY LARVAE

THE PRIOR ART

The production of organic compost from municipal refuse or garbage is well known. For example, U.S. Pat. No. 5,082,486 teaches a method for the production of organic compost comprising the following steps:

1. shredding the refuse;
2. adding water to saturation;
3. adding earthworms;
4. keeping the water content at more than 80% during at least 30 days;
5. keeping the mixture at a temperature from 0°–54° C. and with a moisture of at least 45% during more than 4 months.

Such a method is not suitable for continuous treatment of large amounts of putrescent waste. Furthermore, the separation of earthworms from the treated waste materials is very difficult.

This invention relates to a device and method for the continuous treatment of large amounts of humid putrescent waste materials by means of fly larvae, so that after a relatively short period of a few days, the waste is converted into a more or less dry and odor-free compost. After treatment of the waste materials, the invention also foresees the easy separation of the larvae from the waste. Live or dehydrated larvae constitute an excellent feed stock for fish and poultry, but said larvae can also be used for the production of by-products such as protein meal, chitin and chitosan. It has been observed that when using fly larvae for the treatment of putrescent waste materials, it is possible to induce them to crawl out of the waste by exposing the waste to an illumination, preferably together with a heating, especially an infrared illumination, whereby the separation of the larvae out of the putrescent waste is obtained by the larvae themselves.

BRIEF DESCRIPTION OF THE INVENTION

The invention relates to a device for the treatment of putrescent waste by means of fly larvae, in which the larvae actually eat the waste, said device comprising:

- a conveyor belt consisting of at least a waste reception zone, a waste treatment zone and a waste evacuation zone;
- a means to distribute the waste more or less evenly onto said conveyor belt;
- a means of depositing fly larvae or fly larvae eggs onto the waste;
- a means for removing fly larvae from the waste and from the conveyor belt;
- a means for removing the waste residue from the conveyor belt.

One of the preferred means of removing the fly larvae from the waste and off of the conveyor belt consists of inducing the larvae to crawl out of the waste and off of the conveyor belt by means of a graduated application of light or heat or a combination of both onto the fly larvae and onto the waste. Since fly larvae are negatively phototropic, and since they are uncomfortable or may even die at high temperatures, they can be induced to crawl toward one or both of the lateral edges of the conveyor belt. Preferably they can be induced to crawl toward one or both lateral edges of the conveyor belt by means of a graduated series of lamps. For example tests have shown that infrared lamps are very effective in this regard.

The graduated application of light and heat advantageously creates a zone in which a temperature higher than the temperature of the treatment zone of the waste is reached, said temperature being for example 5° to 25° C., preferably 10° to 15° C., higher than the temperature of the treatment zone. Said zone has a front line through which the waste enters by means of relative motion between the conveyor belt and the means for gradually applying light and heat. Said front line has at least one curved and/or inclined section with respect to the direction of the motion of the conveyor belt, so that the larvae are induced to crawl towards one or both of the lateral edges of the conveyor belt.

Preferably the means to distribute the waste does not distribute the waste over the entire width of the conveyor belt. This leaves the two lateral edges of the conveyor belt free of waste. The width of said lateral edge free of waste is preferably at least twice the maximum length of the fly larvae being induced to crawl out of the waste. The two lateral edges of the conveyor belt are left free of waste, so that as the fly larvae crawl out of the waste, any particles of waste adhering to the fly larvae might become detached from the fly larvae as they crawl toward the lateral edge of the conveyor belt. Said lateral edge may be provided with means for improving the detachment of waste particles from the fly larvae. Pins, needles, bristles, holes and indentations within or upon the conveyor belt are example of such means.

Upon arriving at the edge of the conveyor belt, the fly larvae are further induced by light and/or heat to crawl entirely off of the surface of the conveyor belt, thereupon failing or sliding directly into a fish pond or a hen house wherein they would be immediately consumed. Preferably the fly larvae would fall or slide off of the conveyor belt into a fly larvae collection and evacuation system, which may consist of a trough into which the larvae slide or fall, said trough being provided with a system for creating a stream of water for transporting the fly larvae along the bottom of the trough. In said preferred embodiment, the device advantageously further comprises a screen, trommel or sieve for the rinsing and dewatering of the fly larvae.

Several such fly larvae cultivation belts can be stacked one above the other, and several conveyor belt stacks can be situated in a single chamber. The temperature and humidity within this fly larvae cultivation chamber can be controlled so as to create an atmosphere ideally suited for the fastest growth rate of the larvae.

The invention relates also to a method for the continuous treatment waste by means of fly larvae, in which larvae eat the waste, said method comprising the following steps:

- discharging and more or less evenly distributing putrescent waste onto a conveyor belt;
- depositing fly larvae eggs or fly larvae onto the waste;
- ensuring the hatching of the eggs;
- ensuring a minimum residence time of the larvae in the waste so that all of the waste is eaten and so that the majority of the fly larvae reach maturation;
- exposing a part of the waste to light and/or heat, in such a way that the larvae crawl out of the waste and off of the lateral edge of the conveyor belt;
- removing the waste from the conveyor belt.

Details and characteristics of the invention will appear from the following description in which reference is made to the attached drawings.

BRIEF DESCRIPTION OF THE DRAWINGS

FIG. 2 is an plan view of the conveyor belt system of a device of the invention.

FIG. 3 is a side view of the conveyor belt system of a device of the invention

FIG. 4 is a cross section view of the conveyor belt system along the line IV—IV.

DESCRIPTION OF A PREFERRED EMBODIMENT OF THE INVENTION

Figure 1:
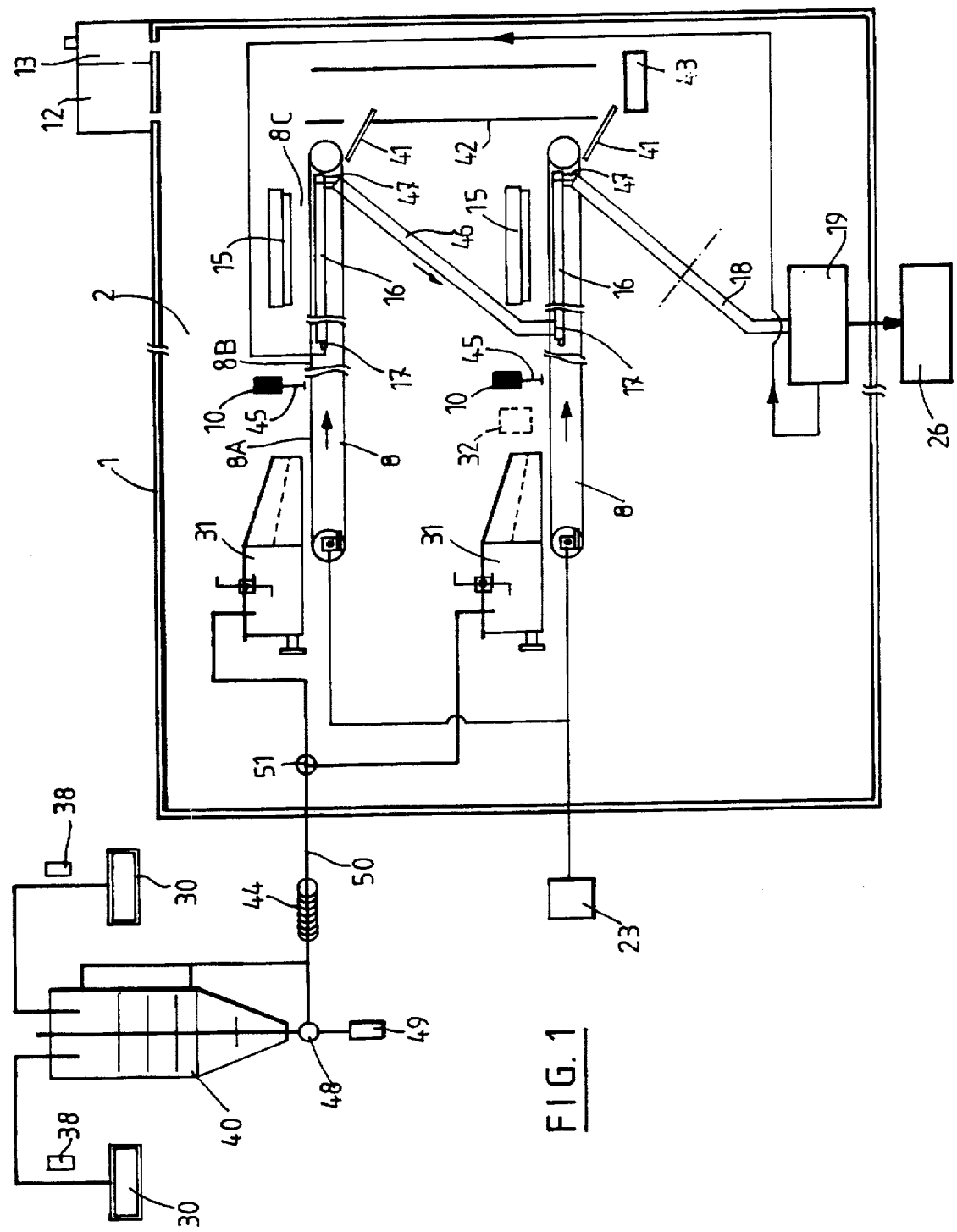
FIG. 1 is a flow diagram of a first embodiment of a device of the invention.

FIG. 1 is a flow diagram of a device (given as example only) for continuous treatment of putrescent waste by means of fly larvae, in which said fly larvae actually eat the waste. The device comprises:

- walls 1 defining a fly larvae cultivation chamber 2 for the treatment of putrescent waste;
- a stack of conveyor belt systems 8, each having a waste reception zone 8A, a treatment zone 8B in which the putrescent waste is more or less completely eaten by fly larvae, and an evacuation zone 8C, the said conveyor belts designed so as to transport the waste and the fly larvae eating the waste from the reception zone 8A towards the evacuation zone 8C;
- a system 30 for grinding putrescent waste material to be treated so as to form a pulp containing particles of a more or less uniform grain size, the grain size being preferrably smaller than the size of the adult fly larvae mouth;
- a blending and holding tank 40 for the ground putrescent waste;
- a pump 48 to transfer the waste from the blending and holding tank 40 to the paddle box 31;
- a variable speed control system 49 for pump 48 to control the discharge rate of waste into the paddle box 31;
- a pipe 50 to transfer the ground waste from the pump 48 into the paddle box 31, said pipe being provided with a heating system 44;
- a valve 51 mounted on pipe 50 to select sequentially the specific paddle box and conveyor belt which are to receive the waste;
- a distribution box 31 with paddles so as to ensure a more or less even deposition of the ground putrescent waste onto the central section of the conveyor belt, leaving the lateral surfaces 8D, 8E of the conveyor belt adjacent to the lateral edges 8F, 8G free of waste;
- one or more distribution bags (baxters)10 containing an aqueous suspension of fly larvae eggs, said bags 10 being made preferably of plastic, and being connected to one or more tubes 45 through which the suspension liquid containing eggs drops onto the waste exiting the paddle box;
- a motor and speed reducer 11 for driving the conveyor belt 8, said motor being associated with a system for controlling the speed of the conveyor belt 8;
- an air-conditioning system 12 to control the most appropriate temperature, humidity and oxygen content in the fly larvae cultivation chamber (for example, between 28°–38° C., between 30–90% relative humidity), depending on the species of fly larvae used;
- an air-scrubbing system 13 to deoderise the leaving the fly larvae cultivation chamber;
- infrared lamps 15 located in the evacuation zone 8C for inducing the larvae to crawl out of the waste;
- two troughs 16, one on each lateral side of the conveyor belt, for collecting and transporting the larvae falling or sliding from the conveyor belt 8, each trough 16 having a water inlet 17 so as to create a water stream for transporting the larvae out of the trough, as well as an outlet 47 for evacuating the water and fly larvae;
- a transfer pipe 46 connecting the outlet 47 of a first conveyor belt trough to the inlet 17 of a second conveyor belt trough, said second conveyor belt preferrably being situated below the first;
- a pipe 18 through which the water stream with larvae flows toward a central rinsing and dewatering device 19, for example vibratory de-watering screen;
- a conveyor belt scraper 41 for scraping and cleaning the conveyor belt, and for transfering the fly larvae residue onto a chute 42;
- a centralised conveyor belt 43 for receiving waste from one or more waste chutes 42;
- a storage area or surge bin for receiving the waste from conveyor belt 43;
- a variable speed control system 23 to determine the speed or the intermittent movement of the conveyor belt (for example if the larvae in the evacuation zone have not reach optimal maturation, the speed of the conveyor belt could be reduced so as to increase the residence time of the larvae on the conveyor belt);
- possibly a system 32 measuring the thickness of the waste deposited on the conveyor belt and controlling the amount of eggs or larvae to be added to the waste, so that the appropriate amount of eggs or larvae is added according to the thickness of waste on the belt, the said system controlling for example the outlet of eggs or larvae from the distribution box 10;
- possibly a system 38 for determining the presence of heavy metals or other contaminants in the waste, said system preventing the entry of contaminated waste into the blending and holding tank 40.

The paddle box 31 ensures an even deposition of the waste on the conveyor belt, but not over the entire width of the conveyor belt. This leaves the lateral surfaces 8D, 8E of the conveyor belt adjacent to the lateral edges 8F, 8G free of waste. Said lateral surfaces 8D, 8E are preferrably about 10 cm in width and are provided with pins, needles, bristles, indentations or holes, all of which may serve as a means for improving the detachment of waste particles adhering to the larvae crawling off of the conveyor belt.

Upon reaching maturity, fly larvae naturally crawl out of the waste, but since they do not all reach maturity at exactly the same time, infrared lamps 15 are used for inducing the fly larvae to crawl out of the waste and off of the conveyor belt in a synchronised and orderly manner. Even the direction in which the fly larvae crawl can be controlled by means of the graduated application of light and heat. Said lamps are preferrably mounted in the form of a triangle, with one comer of the triangle intersecting the vertical plane passing through the middle line of the conveyor belt so as to induce the fly larvae to crawl left and right of said middle line. When the conveyor belt is in motion, preferrably all the lamps within the triangle are "on". While when the conveyor belt in not on motion, preferrably only some of the lamps are "on", effectively providing a barrier across which the fly larvae would be reluctant to crawl.

Said lamps 15 create a zone in which a temperature higher than the temperature of the treatment zone 8B is reached, said temperature being 5° to 25° C. (for example 10°–5° C.) higher than the temperature in the treatment zone. Said zone has a front line (F) through which the waste enters by means of a motion (M) of the conveyor belt, said front line (F)

being adapted with respect to the direction of the motion (M) of the conveyor belt 8 so that the larvae are induced to crawl © towards the lateral edge 8F or towards the lateral edge 8G of the conveyor belt. The fly larvae evacuation trough 16 also serves as means for washing or rinsing the larvae. The larvae collected in the trough 16 can be sold as live fly larvae, but preferably they are further treated in an plant 26 for producing protein meat, chitin, chitosan and other valuable products.

The preparation of eggs can be ensured by female flies induced to lay eggs in an egg deposition chamber, for example onto a surface especially prepared for this purpose. By rinsing this surface, it is possible to collect the eggs in the form of an aqueous egg suspension. Said suspension may be temporarily stored and transported in sealed plastic bags or baxters.

The waste to be treated, when solid, is preferably ground before treatment in a device according to the invention. The grinding is preferably such that the particle size of the particles possibly adhering onto the larvae crawling out of the waste is low enough that these particles can be easily rinsed and screened off of the fly larvae by means of an appropriate rinsing and dewatering device.

Some examples of the kinds of putrescent waste which can be treated are: wasted human food, food waste from canneries and slaughter houses, animal sewage, human sewage sludge, etc. Since the fly larvae grows from egg to pupae in just two to four days, depending on the species of fly being used, the waste processing and disposal time is extremely rapid compared to classical composting techniques. After eating and tunneling their way through the waste over several day, the fly larvae leave behind a relatively dry residue which serves ideally as a compost. This compost can be mixed with water so as to form a pulp suitable for further treatment by means of fly larvae or earthworms.

By means of the device of FIG. 1, the following method of treatment can be effected. The treatment is continuous in the sense that the waste material is continuously treated by means of the fly larvae between the reception zone and the the evacuation zone, yet the conveyor belt 8 does not have to be continuously in motion. It is often desirable to stop the conveyor belt for a specified period of time so as to ensure a sufficient residence time of the waste to be treated on the conveyor belt.

A method of treatment of putrescent waste is disclosed hereafter:

Said method comprises the following steps:

discharging and more or less evenly distributing putrescent waste onto a conveyor belt having two lateral edges;

ensuring a continuous or intermittent movement of the conveyor belt;

depositing fly larvae eggs onto the waste;

ensuring the hatching of the eggs into larvae by means of an appropriate temperature and moisture ensuring a minimum residence time of the larvae in the waste so that substantially all of the putrescent waste is eaten by the fly larvae and so that the majority of the fly larvae reach maturation;

exposing a part of the waste to light and heat, in such a way that the fly larvae crawl out of the waste and off at least one of the lateral edges of the conveyor belt, said light and heat also serving to partially dehydrate the fly larvae residue;

removing the fly larvae residue from the conveyor belt.

Advantageously, the fly larvae crawling off of the conveyor belt are collected in a trough, a current of water being created in the trough for transporting the collected fly larvae to a rinsing and dewatering system, in which the fly larvae are rinsed and dewatered.

Preferably, for removing fly larvae from the waste, light and heat are gradually applied onto the fly larvae and onto the waste. For example, a zone with a temperature higher than the temperature of the treatment zone is created, said temperature being 5° to 25° C., preferably 10° to 15° C., higher than the temperature in the treatment zone.

In a preferred method, said zone has a front line (F) through which the waste enters by means of a motion (M) of the conveyor belt, said front line being adapted with respect to the direction of the motion of the conveyor belt so that the larvae are induced to crawl © towards at least one lateral edge of the conveyor belt, preferably towards the lateral edge 8F or towards the lateral edge 8G.

In the device of FIG. 1, the front line (F) has two sections (F1, F2) which are inclined with respect to the direction of the motion of the conveyor belt. Said sections could possibly be curved with respect to the direction of said motion. The angle between an inclined section and the direction of the motion depends on the speed of movement of the conveyor belt and on the average speed of the crawling of the fly larvae used for eating the waste.

The waste is preferably distributed not over the entire width of the conveyor belt, so as to leave free of waste the two lateral edges of the conveyor belt, as well as the lateral surfaces adjacent to said lateral edges.

The fly larvae crawling out of the waste are then induced to crawl on at least one lateral surface of the conveyor belt which is free of waste. Advantageously, said fly larvae come into contact with one or more means, located on said lateral surface free of waste, so as to detach waste particles adhering to the fly larvae. For example, the fly larvae crawling out of the waste are induced to crawl over a distance of at least ten centimeters free of waste, said distance being at least equal to thrice the maximum length of the fly larvae induced to crawl out of the waste.

Various species of fly larvae can be used for the treatment method. However, it is advisable to select the species the more adapted for eating the waste to be treated. Some species of fly larvae reach a length of 20 to 25 mm at maturation. Since the protein content of fly larvae is greater than 55%, and since the chitin content of the epidermis of the fly larvae is greater than 30%, the real commercial value of this treatment method lies not in the compost but in the fly larvae themselves. The simple centrifugation of fly larvae gives simultaneously both protein and chitin, two very valuable products.

In a method according to the invention, fly eggs were placed on finely ground fresh waste in the form of a pulp (water content of the pulp: about 65–75%). The eggs hatched within 24 hours. After about 72 hours, the larvae reach maturation and were induced to crawl off of the conveyor belt. The residue of the waste treated by the larvae has then a water content of less than 20%, for example about 15% by weight. Said residue has furthermore no special odor problem. The waste treatment is preferably made in a substantially closed chamber, since an ammonia odor is present during treatment process.

The thickness of the fresh waste deposited on the conveyor belt is advantageously limited to a few cm, for example from 2 to 4 cm so that the food present at the bottom of the waste is sufficiently available to the larvae. Furthermore, if the waste layer is too thick, the fly larvae present at the bottom would possibly not be induced to crawl out of the waste or would require a too long time period for crawling out of the waste, whereby the speed of movement of the conveyor belt will have to be reduced. A too thick layer of waste will also reduce the speed of treatment, since the oxygen availability at the bottom of the waste will be reduced.

What I claim is:

1. A device for the continuous treatment of waste by means of fly larvae, in which the said fly larvae actually eat the waste, said device comprising:
 a conveyor belt having two lateral edges and consisting of at least a waste reception zone, a waste treatment zone and a waste evacuation zone;
 means to distribute the waste more or less evenly onto said conveyor belt;
 means for depositing fly larvae or fly larvae eggs onto the waste on the conveyor belt;
 means for removing fly larvae from the waste and from the conveyor belt, and comprising means for inducing fly larvae to crawl out of the waste towards at least one lateral edge of the conveyor belt and off the conveyor belt along said at least one lateral edge; and
 means for removing the waste from the conveyor belt.

2. The device of claim 1, in which the means for removing fly larvae from the waste is a means for gradually applying light and heat onto the fly larvae and onto the waste.

3. The device of claim 2, in which the means for removing fly larvae creates a zone in which a temperature higher than the temperature of the treatment zone is reached, said temperature being 5° to 25° C. higher than the temperature in the treatment zone.

4. The device of claim 2, in which the means for removing fly larvae creates a zone in which a temperature higher than the temperature of the treatment zone is reached, said temperature being 10° to 15° C. higher than the temperature in the treatment zone.

5. The device of claim 1, in which the means for removing fly larvae from the waste is a means for gradually applying light and heat onto the fly larvae and onto the waste, so as to create a zone in which a temperature higher than the temperature of the treatment zone is reached, said zone having a front line through which the waste enters by means of a relative motion between the conveyor belt and the means gradually applying light and heat, said front line being adapted with respect to the direction of the motion of the conveyor belt so that the larvae are induced to crawl towards at least one lateral edge of the conveyor belt.

6. The device of claim 1, in which the means for removing fly larvae from the waste is a means for gradually applying light and heat onto the fly larvae and onto the waste, so as to create a zone in which a temperature higher than the temperature of the treatment zone is reached, said zone having a front line through which the waste enters by means of a relative motion between the conveyor belt and the means gradually applying light and heat, said front line being adapted with respect to the direction of the motion of the conveyor belt so that the larvae are induced to crawl towards both lateral edges of the conveyor belt.

7. The device of claim 1, in which the means for removing fly larvae from the waste is a means for gradually applying light and heat onto the fly larvae and onto the waste, so as to create a zone in which a temperature higher than the temperature of the treatment zone is reached, said zone having a front line through which the waste enters by means of a relative motion between the conveyor belt and the means gradually applying light and heat, said front line having at least one section curved with respect to the direction of the relative motion between the conveyor belt and the means gradually applying light and heat, so that the larvae are induced to crawl towards at least one lateral edge of the conveyor belt.

8. The device of claim 1, in which the means for removing fly larvae from the waste is a means for gradually applying light and heat onto the fly larvae and onto the waste, so as to create a zone in which a temperature higher than the temperature of the treatment zone is reached, said zone having a front line through which the waste enters by means of a relative motion between the conveyor belt and the means gradually applying light and heat, said front line having at least one section inclined with respect to the direction of the relative motion between the conveyor belt and the means so that the larvae are induced to crawl towards at least one lateral edge of the conveyor belt.

9. The device of claim 1, in which the means to distribute the waste is adapted for distributing the waste in such a manner so as to leave free of waste the two lateral edges of the conveyor belt, as well as the lateral surfaces adjacent to said lateral edges.

10. The device of claim 9, in which the lateral surfaces of the conveyor belt adjacent to the lateral edges are provided with means for coming into contact with the fly larvae crawling off of the conveyor belt thereby detaching waste particles adhering to the fly larvae.

11. The device of claim 9, in which the width of each lateral surface free of waste is at least equal to twice the maximum length of the fly larvae induced to crawl out of the waste.

12. The device of claim 1, which is provided with a fly larvae collection and evacuation system receiving the fly larvae crawling off the conveyor belt.

13. The device of claim 12, in which the fly larvae collection and evacuation system consists of a trough in which the larvae are collected, said trough having a bottom and being provided with a system for creating a stream of water for transporting the fly larvae, said system being adapted for creating a stream of water at least along the bottom of the trough.

14. The device of claim 1, which is provided with:
 a fly larvae collection and evacuation system receiving the fly larvae crawling off the conveyor belt, the fly larvae collection and evacuation system consisting of a trough in which the larvae are collected, said trough having a bottom and being provided with a system for creating a stream of water for transporting the fly larvae, said system being adapted for creating a stream of water at least along the bottom of the trough, and
 a rinsing and dewatering system for rinsing and dewatering the larvae collected in the stream of water flowing out of the trough.

15. The device of claim 1, which comprises walls forming a chamber in which are located several conveyor belts for the treatment of waste by means of fly larvae, said chamber being provided with means for controlling its temperature and humidity.

16. Method for the continuous treatment of waste by means of fly larvae, in which the said fly larvae actually eat the waste, said method comprising the following steps:
 discharging and more or less evenly distributing putrescent waste onto a conveyor belt having two lateral edges;
 ensuring a movement of the conveyor belt;
 depositing fly larvae eggs onto the waste on the conveyor belt;

ensuring the hatching of the eggs into larvae;

ensuring a minimum residence time of the larvae in the waste so that substantially all the putrescent waste is eaten by the fly larvae and so that the majority of the fly larvae reach maturation;

exposing a part of the waste to light and heat, in such a way that the fly larvae crawl out of the waste and off of the conveyor belt through at least one of its lateral edges, and removing the waste from the conveyor belt.

17. The method of claim 16, in which the fly larvae crawling off of the conveyor belt are collected in a trough, a current of water being created in the trough for transporting the collected fly larvae to a rinsing and dewatering system, in which the fly larvae are rinsed and dewatered.

18. The method of claim 16 in which, for removing fly larvae from the waste, light and heat are gradually applied onto the fly larvae and onto the waste.

19. The method of claim 18, in which, for removing fly larvae from the waste, a zone with a temperature higher than the temperature of the treatment zone is created, said temperature being 5° to 25° C. higher than the temperature in the treatment zone.

20. The method of claim 18, in which, for removing fly larvae from the waste, a zone with a temperature higher than the temperature of the treatment zone is created, said temperature being 10° to 15° C. higher than the temperature in the treatment zone.

21. The method of claim 16, in which, for removing fly larvae from the waste, light and heat are gradually applied onto the fly larvae and onto the waste, so as to create a zone with a temperature higher than the temperature of the treatment zone, said zone having a front line through which the waste enters by means of a relative motion between the conveyor belt and the light and heat applied, said front line being adapted with respect to said relative motion so that the larvae are induced to crawl towards at least one lateral edge of the conveyor belt.

22. The method of claim 16, in which, for removing fly larvae from the waste, light and heat are gradually applied onto the fly larvae and onto the waste, so as to create a zone with a temperature higher than the temperature of the treatment zone, said zone having a front line through which the waste enters by means of a relative motion between the conveyor belt and the light and heat applied, said front line being adapted with respect to said relative motion so that the larvae are induced to crawl towards both lateral edges of the conveyor belt.

23. The method of claim 16, in which, for removing fly larvae from the waste, light and heat are gradually applied onto the fly larvae and onto the waste, so as to create a zone with a temperature higher than the temperature of the treatment zone, said zone having a front line through which the waste enters by means of a relative motion between the conveyor belt and the light and heat applied, said front line having at least one section curved with respect to the direction of said relative motion so that the larvae are induced to crawl towards at least one lateral edge of the conveyor belt.

24. The method of claim 16, in which, for removing fly larvae from the waste, light and heat are gradually applied onto the fly larvae and onto the waste, so as to create a zone with a temperature higher than the temperature of the treatment zone, said zone having a front line through which the waste enters by means of a relative motion between the conveyor belt and the light and heat applied onto the fly larvae and onto the waste, said front line having at least one section inclined with respect to the direction of said relative motion so that the larvae are induced to crawl towards at least one lateral edge of the conveyor belt.

25. The method of claim 16, in which the waste is distributed in such a manner so as to leave free of waste the two lateral edges of the conveyor belt, as well as the lateral surfaces adjacent to said lateral edges.

26. The method of claim 25, in which the fly larvae crawling out of the waste are induced to crawl on at least one lateral surface of the conveyor belt which is free of waste, said fly larvae thereby coming into contact with the said lateral areas free of waste so as to detach waste particles adhering to the fly larvae.

27. The method of claim 25, in which the fly larvae crawling out of the waste are induced to crawl over a distance on at least one lateral area of the conveyor belt which is free of waste, said distance being at least equal to twice the maximum length of the fly larvae induced to crawl out of the waste.

* * * * *